(12) United States Patent
Lozano Fantoba et al.

(10) Patent No.: US 7,702,065 B2
(45) Date of Patent: Apr. 20, 2010

(54) DIGITAL STEREOTAXIC BIOPSY SYSTEM

(75) Inventors: Manuel Lozano Fantoba, Bellaterra (ES); Miguel Ullan Comes, Bellaterra (ES); Melcior Sentis I Criville, Cardedeu (ES); Mokhtar Chmeissani, Barcelona (ES)

(73) Assignees: Consejo Superior de Investigaciones Cientificas, Barcelona (ES); Institut de Fisica d'Altes Energies, Barcelona (ES); Udiat Centre Diagnostics, S.A., Barcelona (ES)

( * ) Notice: Subject to any disclaimer, the term of this patent is extended or adjusted under 35 U.S.C. 154(b) by 188 days.

(21) Appl. No.: 11/572,735

(22) PCT Filed: Jul. 27, 2005

(86) PCT No.: PCT/ES2005/000426

§ 371 (c)(1),
(2), (4) Date: Jan. 26, 2007

(87) PCT Pub. No.: WO2006/024679

PCT Pub. Date: Mar. 9, 2006

(65) Prior Publication Data

US 2007/0195928 A1 Aug. 23, 2007

(30) Foreign Application Priority Data

Jul. 29, 2004 (ES) ................. 200401878

(51) Int. Cl.
*A61B 6/03* (2006.01)
*A61B 6/02* (2006.01)
*A61B 5/05* (2006.01)

(52) U.S. Cl. ........................ 378/41; 600/429

(58) Field of Classification Search .............. 378/4, 378/9, 15, 19, 37, 41, 62, 64, 65, 68, 92, 378/98.8, 98.12, 210, 20; 600/407, 424, 600/425, 427, 429; 250/370.09, 370.12, 250/370.13, 370.01, 370.08; 257/614
See application file for complete search history.

(56) References Cited

U.S. PATENT DOCUMENTS

| 6,055,449 A * | 4/2000 | Navab ............. 600/427 |
| 6,102,866 A | 8/2000 | Nields |
| 6,282,261 B1 | 8/2001 | Mazess |
| 6,560,354 B1 | 5/2003 | Maurer |
| 6,628,977 B2 | 9/2003 | Graumann |

(Continued)

FOREIGN PATENT DOCUMENTS

WO WO9311706 6/1993

(Continued)

*Primary Examiner*—Irakli Kiknadze
*Assistant Examiner*—Anastasia Midkiff
(74) *Attorney, Agent, or Firm*—Peter B. Scull; Kristina M. Kalan; Breenbaum Weinshienk PC

(57) ABSTRACT

The invention relates to a digital system (1) for performing stereotaxic biopsies with a biopsy needle. The inventive system (1) comprises a series of devices which are used to: emit X-rays, detect and transform X-ray photons into electric signáis, position a tissue sample between the X-ray source and the detector, process the electric signáis, and generate images. The system can also be equipped with a series of devices complementary to those mentioned above, as well as a means for positioning the aforementioned devices in two positions and obtaining images in two different orientations.

10 Claims, 4 Drawing Sheets

U.S. PATENT DOCUMENTS

| | | | |
|---|---|---|---|
| 6,953,935 B1 * | 10/2005 | Hoffman | 250/370.13 |
| 7,085,343 B2 * | 8/2006 | Shinno et al. | 378/9 |
| 7,453,976 B1 * | 11/2008 | Yin | 378/9 |
| 7,567,648 B2 * | 7/2009 | Tsubaki et al. | 378/41 |
| 2003/0076927 A1 * | 4/2003 | Nakashima et al. | 378/65 |
| 2004/0217294 A1 * | 11/2004 | Zur | 250/370.09 |
| 2005/0020902 A1 * | 1/2005 | Janes | 600/407 |
| 2005/0023475 A1 | 2/2005 | Li | |
| 2005/0175148 A1 * | 8/2005 | Smither | 378/84 |
| 2005/0226364 A1 * | 10/2005 | Bernard De Man et al. | 378/9 |
| 2006/0011853 A1 * | 1/2006 | Spartiotis et al. | 250/370.13 |
| 2006/0180771 A1 * | 8/2006 | Jing et al. | 250/370.14 |

FOREIGN PATENT DOCUMENTS

| | | |
|---|---|---|
| WO | WO2004064168 | 7/2004 |

* cited by examiner

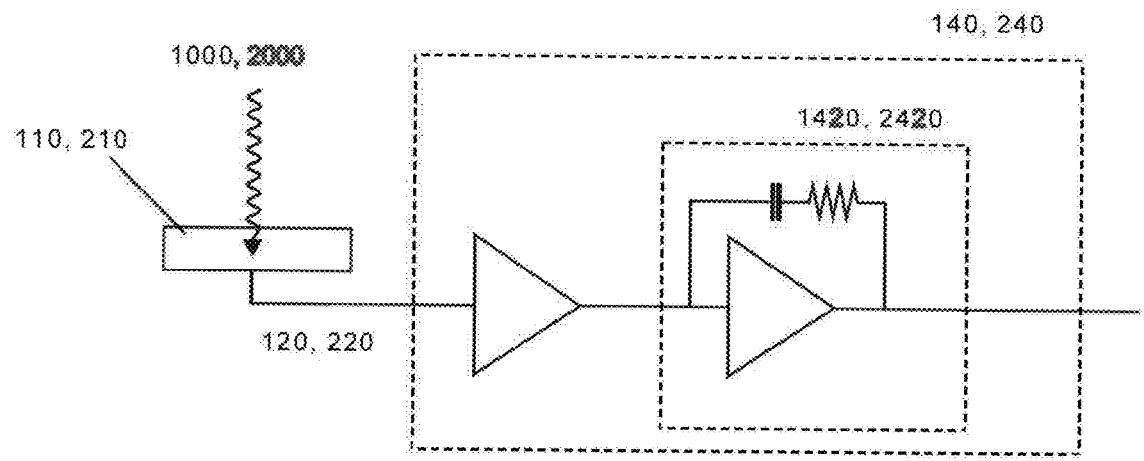
FIG. 5
FIG. 6
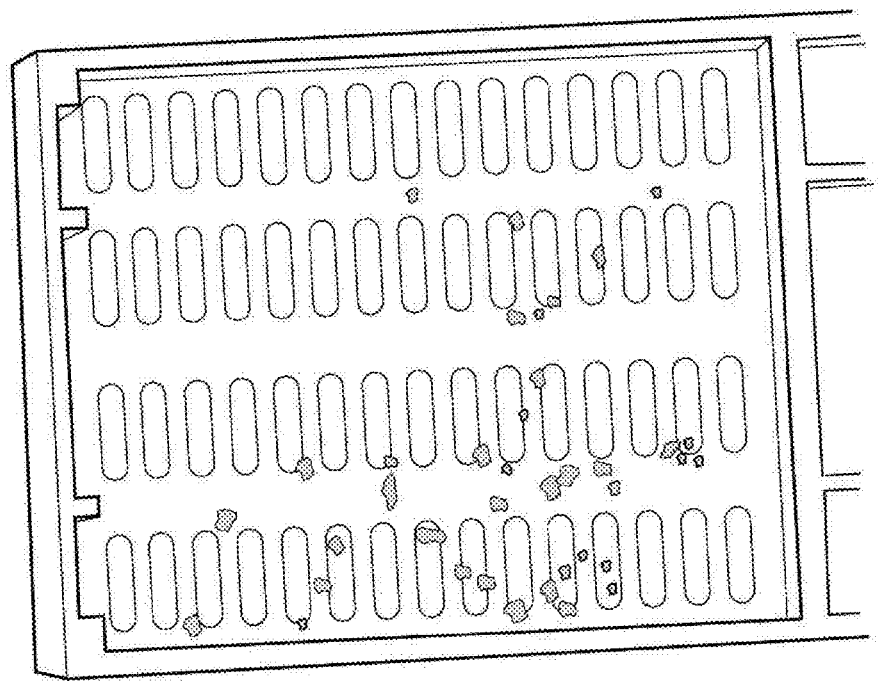

DIGITAL STEREOTAXIC BIOPSY SYSTEM

FIELD OF THE INVENTION

The invention consists of a digital system to guide the biopsy sample-taking process by x-ray imaging.

BACKGROUND OF THE INVENTION

The current biopsy equipments are based on static images that are calculated in a deferred manner and forces the blind placement of a biopsy needle and then check that the needle has been correctly inserted; in the case in which the needle has not been inserted correctly, a new calculation is required to correct the position and a new image or images have to be taken for checking.

The nearest state of the art is made up of systems to carry out radiography that use detectors based on CCD (charge coupled devices).

The current biopsy systems are based on a system of two static images taken at different angles, from which the three dimensional coordinates can be calculated for the lesion that requires analysis or removal. The current systems are not capable of providing information on the position of the device during the insertion of the same that allows its relocation to reach the lesion without mistakes, but force it to be calculated after full insertion; that is, during the guiding of the sample-taking needle, different static images are taken to check the position of the needle. Therefore these systems do not provide a real time image of the needle and sample and do not take into account the elasticity of the tissues or the changes of position from the previous biopsy samples; this carries with it the loss of precision in the taking of biopsy samples that can compromise the final result.

By means of the images thus obtained the stereotaxic technique can be applied; Stereotaxy (from the Greek: stereo, three dimensional; taxis, positioning): a surgical technique that allows the localisation and precise access to internal structures by means of a small opening by using three dimensional coordinates obtained from two radiological images taken in accordance with projections from two angles, axial tomography or magnetic resonance.

The problems to be solved by the present invention include:

enabling the specialists who carry out the biopsies to guide the sample-taking needle in real time, with greater precision, more reliability, more quickly and with less trauma for the patient, making the biopsy sample-taking process more effective in terms of cost;

providing a quick system and in real time that enables the doctors to use short term contrasts or markers to enhance the image;

taking samples of very small lesions or with low contrast.

SUMMARY

The present invention provides a system (1) for performing stereotaxic biopsies with a biopsy needle. The inventive system (1) comprises a series of devices which are used to: emit X-rays, detect and transform X-ray photons into electric signals, position a tissue sample and the biopsy needle between the X-ray source and the detector, process the electric signals, and generate images to guide the biopsy process, with the capability of real-time operation. The system can also be equipped with a series of devices complementary to those mentioned above, as well as a means for positioning the aforementioned devices in two positions and obtaining images in to different orientations.

BRIEF DESCRIPTION OF THE DRAWINGS

Below is a very brief description of a series of drawings that will help to give a better understanding of the invention and that is expressly connected to an embodiment of said invention that is shown by way of example is not by way of limitation on it.

FIG. 5 shows a reading means by means of charge integration.

FIG. 6 shows a static image of grains of salt inside a pathology case.

DESCRIPTION OF A PREFERRED EMBODIMENT OF THE INVENTION

Next, a series of definitions of the concepts used in the description of the present invention will be included.

Indirect conversion: procedure for the capturing of x-rays in which the x-ray photons are converted into visible photons, then being detected by a video camera or similar circuit, where they are converted into an electrical signal.

Direct conversion: procedure for the taking of x-rays in which the x-ray photons are converted into an electrical charge that is gathered in a suitable electronic circuit.

Photon Counting: Method for reading the signal from the x-ray detector by which each photon is converted into a current pulse. If the pulse amplitude exceeds a pre-established threshold, the circuitry increases the counting of the number of photons by one unit. If the electronic noise is below the lower counting threshold, it will not affect the final result.

Charge integration: Method for reading the signal from the x-ray detector by which each photon is converted into a certain amount of electrical charge, proportional to its energy that is stored in a capacitor. Every time a new photon arrives, the charge increases. In addition, the charge stored goes on increasing constantly due to the electronic noise; hence it is necessary to put the capacitor at zero periodically. In this case, it may be more advisable to choose the photon counting solution.

Pixel-Type Detector: Detector formed by element detector units arranged in the form of a bi-dimensional array that will form each one of the elements of the final image.

Figure 1:
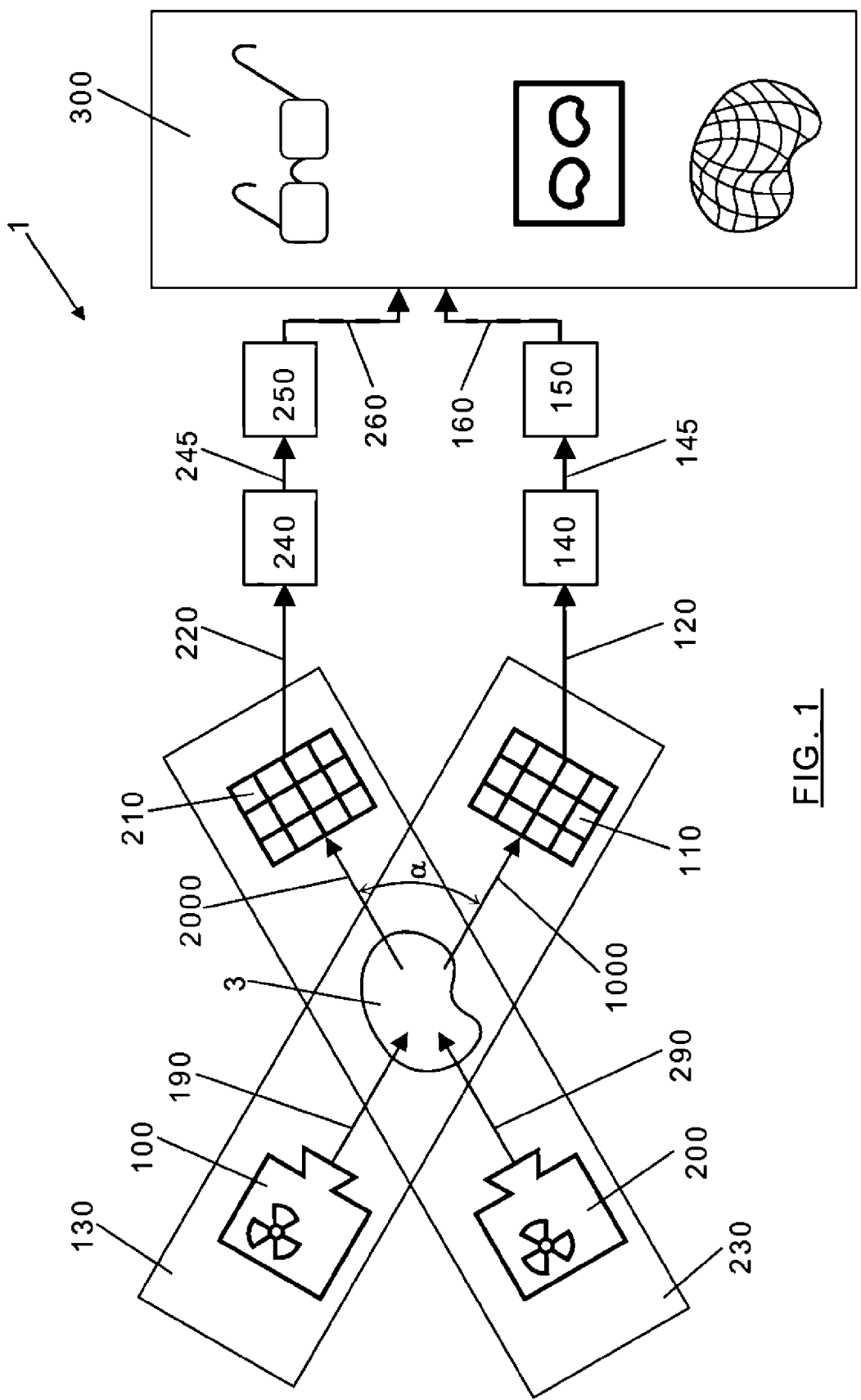
FIG. 1 shows a general scheme of the system of the invention fitted with first and second means, detectors and sources.

A first aspect of the invention refers to a digital system (1) to carry out stereotaxic biopsies with a biopsy needle, said system (1) comprising (see FIG. 1):

a first x-ray source (100);

a first pixel-type detector (110) to convert the x-ray photons (1000) emitted by the first x-ray source (100) into the first electrical signals (120);

a first positioning means (130) to locate a tissue sample (3) between the first x-ray source (100) and the first detector (110):

a first processing means (140) in order to process the first electrical signals (120) of the first detector (110) and to produce the first processed signals (145);

a first imaging means (150) to generate a first image (160) from the first processed signals (145), and a second x-ray source (200);

a second pixel-type detector (210) to convert the x-ray photons (2000) emitted by the second x-ray source (200) into second electrical signals (220);

a second positioning means (230) to locate a tissue sample (3) between the second x-ray source (200) and the second detector (210);

a second processing means (240) to process the second electrical signals (220) of the second detector (210) and produce the second processed signals;

a second imaging means (250) to generate a second image (260) from the second processed signals.

Figure 3:
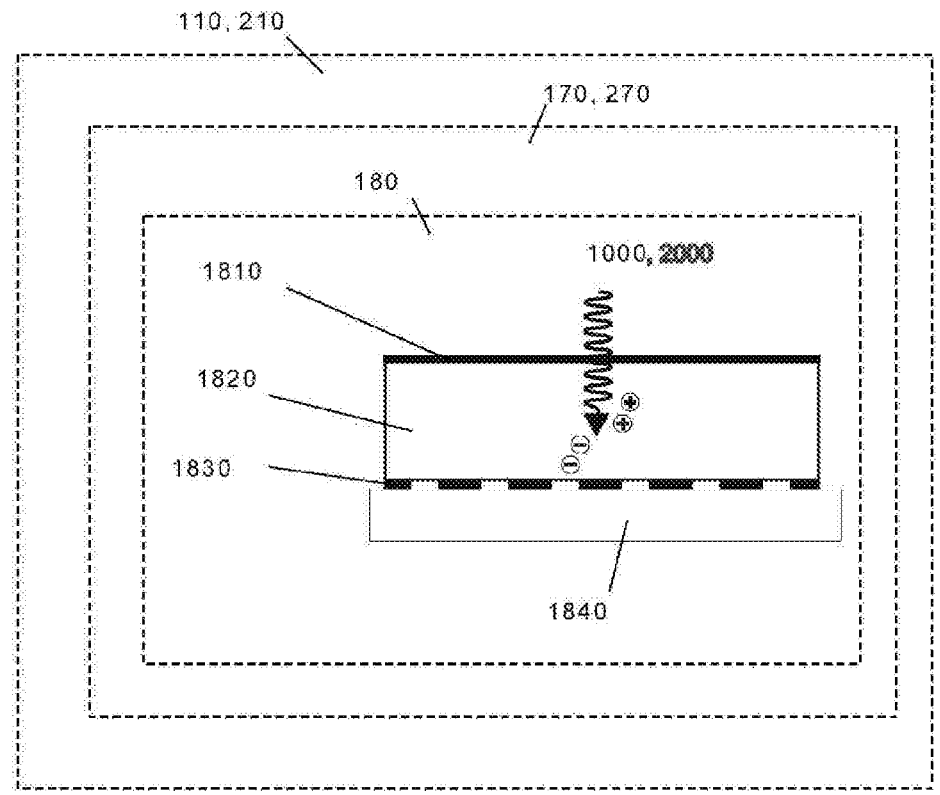
FIG. 3 shows the components of the conversion means.

The system (1) in accordance with the first aspect of the invention is characterized in that:

said first detector (110) includes a first conversion means (170) (see FIG. 3) to carry out a direct conversion of the x-ray photons into an electrical charge;

said second detector (210) includes a second conversion means (270) (see FIG. 3) to carry out a direct conversion of the x-ray photons into an electrical charge;

the first detector (110) and the first x-ray source (100) are aligned on the first axis (190);

the second detector (210) and the second x-ray source (200) are aligned on the second axis (290);

said second axis (290) forms an angle alpha ($\alpha$) with the first axis (190); the system (1) having some means for establishing the alpha ($\alpha$) angle by the user;

a graphical representation (300) of the images (160, 260) is obtained and presented in real time.

A second aspect of the invention makes reference to digital system (2) to carry out stereotaxic biopsies with a biopsy needle, said system having (see FIG. 2):

an x-ray source (100);

a pixel-type detector (110) to convert the x-ray photons (1000) emitted by the x-ray source (100) into the first electrical signals (120);

a positioning means (130) to locate a tissue sample (3) between the x-ray source (100) and the detector (110):

a processing means (140) in order to process the first electrical signals (120) of the detector (110) and to produce the first processed signals (245);

an imaging means (150) to generate a first image (160) from the first processed signals (120).

Figure 2:
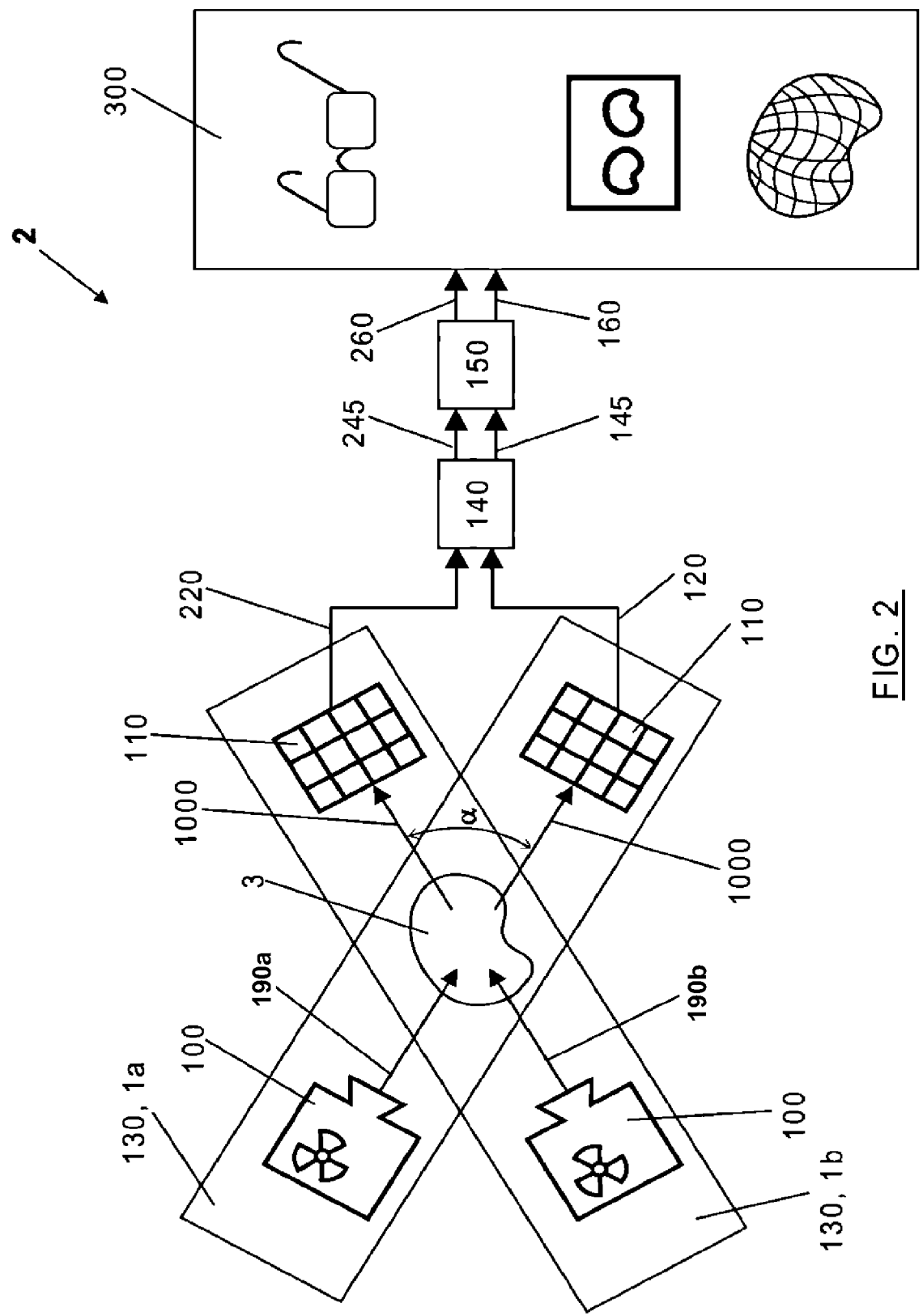
FIG. 2 shows a general scheme of the system of the invention fitted with first means, detectors and sources. The figure shows the components in a first position and a second position.

The system (2) in accordance with the second aspect of the invention is characterized in that:

said detector (110) includes a conversion means (170) (see FIG. 3) to carry out a direct conversion of the x-ray photons into an electrical charge;

the detector (110) and the x-ray source (100) are aligned on an axis (190; which includes the two representations 190a and 190b as shown and represented in FIG. 2 by reference numerals 190a and 190b corresponding to first and second directions (1a and 1b) described further below);

the positioning means (130) are arranged to allow the axis (190; again, as represented in FIG. 2 by reference numerals 190a and 190b corresponding to first and second directions (1a and 1b) described further below) to be moved between:

a first position in accordance with a first direction (1a); and a second position in accordance with a second direction (1b);

that forms the angle alpha ($\alpha$) with the first direction;

the system having some means for establishing the angle alpha ($\alpha$) by the user so that in said second direction (1b):

the pixel-type detector (110) converts the x-ray photons (1000) emitted by the x-ray source (100) into second electrical signals (220);

the processing means (140) process the second electrical signals (220) of the detector (110) and produce the second processed signals (245);

the imaging means (150) generate a second image (260) from the second signals (245) processed by the processing means (140);

a graphical representation (300) of the images (160, 260) is obtained and presented in real time.

Due to the use of a direct conversion in the present invention, a conversion in the photon wavelength is avoided; it is not necessary to pass the x-ray photons into a visible spectrum. By means of the system of the invention described above the problems existing in the current state of the art technique are solved:

allowing the specialists who carry out biopsies to guide the sample-taking needle in real time, with greater precision, more reliability, more quickly and with less trauma for the patient, making the biopsy sample-taking process more effective in terms of cost;

providing a quick system and in real time that enables the doctors to use short term contrasts or markers to enhance the image;

taking samples of very small lesions or with low contrast.

The system of the invention provides a real time image of the needle and the sample, taking into account the elasticity of the tissues and the changes of position from the previous biopsy samples.

In accordance with a first embodiment of the invention, $0° \leq alpha(\alpha) \leq 180°$. Specifically, in a preferred embodiment alpha ($\alpha$)=30°.

In accordance with a second embodiment of the invention, the system includes means for viewing the three dimensional images created from two images selected among:

a monitor with two orthogonal projections;

3D reconstruction;

stereoscopic glasses;

and combinations of the three.

In accordance with a third embodiment of the invention, the system includes 3D generation means for stereotaxic reconstruction of a trajectory of the needle and the position of the lesion from the two images, in order to guarantee that the position of the lesion is going to be intersected by the trajectory of the needle.

In accordance with a fourth embodiment of the invention the intersection of the trajectory with the lesion is shown by visual markers means.

In accordance with a fifth embodiment of the invention, two orthogonal projections are generated from the two images.

In accordance with a sixth embodiment of the invention, a graphical representation of the images is obtained and presented with a minimum refresh rate of at least one image per second.

In accordance with a seventh embodiment of the invention, at least one source of x-rays includes pulse generator devices to work in a pulsed mode with an exposure period of less than half of the image refresh frequency.

Figure 4:
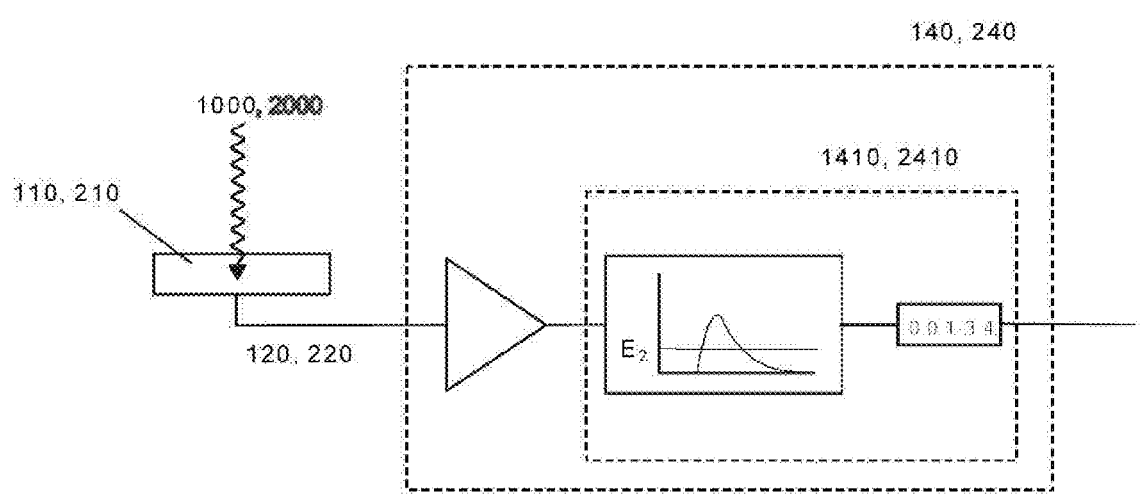
FIG. 4 shows the reading means by photon counting.

In accordance with an eighth embodiment of the invention (see FIG. 4), the processing devices (140, 240) have means (1410, 2410) for reading the electrical signals (120, 220) via photon counting.

In accordance with a ninth embodiment of the invention (see FIG. 5), the processing devices (140, 240) have means (1420, 2420) for reading the electrical signals (120, 220) via charge integration.

In accordance with a tenth embodiment of the invention (see FIG. 3), the conversion means has a semiconductor device (180).

In accordance with an eleventh embodiment of the invention the semiconductor device (180) can operate at room temperature.

In accordance with a twelfth embodiment of the invention (see FIG. 3), the semiconductor device (180) has an upper electrode (1810), lower electrodes (1830), a semiconductor material (1820) between the upper electrode (1810) and the lower electrodes (1830), and electronic read out elements (1840).

The system of the invention is particularly suitable for application in breast biopsy, where there is greater difficulty on dealing with soft and moveable tissue.

Even though the nearest state of the art techniques claim that they provide a real time image, they have limitations in the acquisition of the images and in the quality of the images per second, as they are only capable of obtaining an image every two seconds, in addition the efficiency in the detecting of lesions is questionable because of the type of detector that they use, which is based on CCD. With CCD detectors (indirect conversion), the greatest disadvantage is the number of images per second that can be obtained, as the maximum number achievable is very low. In order to increase this number of images per second, it is necessary to increase the radiation, which is harmful for the health of the patient, as the radiation dose to which they are going to be exposed is too high.

A preferred embodiment of the invention proposes a detector with the possibility of working at room temperature, a solid state detector coupled to an electronic reading system that allows up to 100 images per second to be read. This device can have the capability of detecting any photon, which allows low radiation doses to be worked with. The type of electronics used has a minimum noise providing high quality images. The system can be expanded using more than one radiation source to obtain a real 3D image that can be needed by some special applications (Central Nervous System biopsies (SNC biopsies) or biopsies on other parts of the human body). One test carried out using the Lorad (Stereolock) biopsy system as a mechanical platform and using a commercial detector based on CdTe (Cadmium Tellurium) allowed higher quality images to be obtained than the conventional ones, using exposures of 20 mSec and reducing the x-ray flux with a 1 mm Aluminum (Al) filter.

The working principle is based on the radioscopy principles used in other applications being in the case of the present invention specially used for small areas that require the greater resolution necessary in the radiological image such as mammary lesions. This is possible using the technology with solid state detectors at room temperature and electronic technology.

The system of the present invention is sufficiently simple to be able to add it to any already existing biopsy machine and the means to control it can be adapted to the known systems controlling the x-ray source and capturing images, with the required synchronization of the X-ray tube emission and sensor acquisition.

The parts of a preferred embodiment of the invention are:
a 50×50 mm detector assembled on a card that is adapted to all types of biopsy machines.

a communication means to send the data from the detector to the machine that controls the existing biopsy system controlled by specific controlling means, in order to synchronize the x-ray system and the detector.

As it was mentioned in a previous paragraph, the system allows to be incorporated into the existing machines in the simplest manner. In accordance with another preferred embodiment of the invention, the system includes multiple sources of radiation that allow a real three dimensional image system to be able to be applied to other types of biopsies or medical applications.

At the point of carrying out the biopsy because of the nature of the tissue or of the lesion itself, it makes the object to move. With the known systems it is only possible to know by taking images after the final introduction or, in some cases, with the report of the biopsy from the pathologist, giving an non conclusive result.

The system of the present invention allows the biopsy to be taken at the first try ensuring the taking of the sample and avoiding repetitions either because of bad positioning or unsuitable sampling, allowing the biopsy times to be reduced, making it more efficient and allowing more samples to be done in a reasonable time.

By means of the present invention system, the radiation dose used in the whole procedure is equivalent to that used in a static image. This advantage is illustrated in FIG. 6 where a static image of salt grains is shown inside of a pathology case. Said figure shows the resolution at low dose, which is estimated at 0.3 mAs; whereas the static image by means of the known systems is obtained with a minimum exposure of 80 mAs, which means that the reduction of the dose with the system used in the present invention is 250 times for that image.

The invention claimed is:

1. A digital system to assist in carrying out stereotaxic breast biopsies with a biopsy needle to provide for visualization of the position of said biopsy needle with respect to the breast in real-time, said system comprising:
an x-ray source for emitting x-ray photons;
a pixel-type detector to convert the x-ray photons emitted by the x-ray source into first electrical signals;
a positioning means to locate a tissue sample between the x-ray source and the pixel-type detector;
processing means in order to process the electrical signals of the pixel-type detector and to produce processed signals; and
imaging means to generate a two-dimensional image from said processed signals;
wherein:
said pixel-type detector includes conversion means to carry out a direct conversion of the x-ray photons into an electrical charge; and
said pixel-type detector—and the x-ray source are aligned on a working axis
the positioning means are arranged to allow the movement of the working axis between a first position in accordance with a first direction and a second position in accordance with a second direction that forms an angle α with the first direction, wherein $0° \leq \alpha \leq 180°$; and wherein,
the system includes means to set the angle α by the user; and
display means to display the two-dimensional images generated with the imaging means, said display means including a monitor with two projections for displaying two images simultaneously, the imaging means generating a first image in the first position and generating a second image in the second position, the monitor displaying the first image and the second image in real time, such that a three-dimensional visualization is provided to and visualized by a specialist wearing stereoscopic glasses.

2. The system in accordance with claim 1 further including 3D generation means to stereotaxically reconstruct a needle trajectory and a position of a lesion from the first image and the second image to guarantee that the position of the lesion will be intersected by the needle trajectory.

3. The system in accordance with claim 2 wherein intersection of the needle trajectory with the lesion is shown by means of visual markers.

4. The system in accordance with claim 1 wherein a graphical representation of the first image and the second image is obtained and presented with a minimum refresh rate of at least one image per second.

5. The system in accordance with claim 4 wherein the x-ray source comprises means for pulse generation to work in pulsed mode with an exposure period of less than one half of the image refresh rate frequency.

6. The system in accordance with claim 1 wherein the processing means has a means for reading the electrical signals by means for photon counting.

7. The system in accordance with claim 1 wherein the processing means has means for reading the electrical signals by means of charge integration.

8. The system in accordance with claim 1 wherein the conversion means has a semiconductor device.

9. The system in accordance with claim 8 wherein the semiconductor device can be operated at room temperature.

10. The system in accordance with claim 9 wherein the semiconductor device has an upper electrode, lower electrodes, a semiconductor material between the upper electrode and the lower electrode, and electronic read out elements.

* * * * *